United States Patent [19]

Sofianos

[11] Patent Number: 5,254,520

[45] Date of Patent: Oct. 19, 1993

[54] CATALYST FOR THE SYNTHESIS OF METHANOL

[75] Inventor: Alkeos Sofianos, Pretoria, South Africa

[73] Assignee: CSIR, Pretoria, South Africa

[21] Appl. No.: 761,715

[22] Filed: Sep. 17, 1991

[30] Foreign Application Priority Data

Sep. 18, 1990 [ZA] South Africa ............... 90/7437

[51] Int. Cl.$^5$ .............. B01J 21/04; B01J 21/06; B01J 23/06; B01J 23/28; B01J 23/34; B01J 23/72

[52] U.S. Cl. .................. 502/307; 502/324; 518/713

[58] Field of Search .............. 502/307, 324, 342; 518/713

[56] References Cited

U.S. PATENT DOCUMENTS

| | | | |
|---|---|---|---|
| 3,326,956 | 6/1967 | Davies et al. | 260/449.5 |
| 4,107,089 | 8/1978 | Bondar et al. | 502/307 |
| 4,483,943 | 11/1984 | Windawi et al. | 502/342 |
| 4,537,876 | 8/1985 | Blum et al. | 502/342 |
| 4,666,945 | 5/1987 | Osugi et al. | 502/342 X |
| 4,843,101 | 6/1989 | Klier et al. | 518/713 |

FOREIGN PATENT DOCUMENTS

| | | |
|---|---|---|
| 1930702 | 1/1971 | Fed. Rep. of Germany. |
| 2154074 | 5/1972 | Fed. Rep. of Germany. |
| 2514665 | 4/1983 | France. |
| 8600545 | 1/1986 | PCT Int'l Appl.. |
| 1159035 | 7/1969 | United Kingdom. |
| 1296212 | 11/1972 | United Kingdom. |
| 1302726 | 1/1973 | United Kingdom. |
| 1405012 | 9/1975 | United Kingdom. |
| 2025252 | 1/1980 | United Kingdom. |
| 2025418 | 1/1980 | United Kingdom. |
| 2037176 | 7/1980 | United Kingdom. |
| 2047556 | 12/1980 | United Kingdom. |
| 2064352 | 6/1981 | United Kingdom. |
| 2109263 | 6/1983 | United Kingdom. |
| 2151498 | 7/1985 | United Kingdom. |

OTHER PUBLICATIONS

V. V. Lunin et al., "Methanol Synthesis from CO and $N_2$ on Zr/Cu Catalysts", Kinetics & Catalysts vol. 28(1), 1987, pp. 90–192.

M. Shimokawabe et al., "Characterization of Copper/Zirconia Catalysts Prepared by an Impregnation Method", Applied Catalysis, 59, 1990, pp. 45–58.

G. J. J. Bartley et al., "Support and Morphological Effects in the Synthesis of Methanol over Cu/ZnO, Cu/ZnO$_2$ and Cu/SiO$_2$ Catalysts", Applied Catalysis 43, 1988, pp. 141–153.

James Crocco, "Methanol: Yesterday, Today, and Tomorrow", Chemistry & Industry, 1990, pp. 97–101.

G. C. Chinchen et al., "Review—Synthesis of Methanol", Applied Catalysis, 36, 1988, pp. 1–65.

Z. Xu et al., "Methanol Synthesis from $CO_2$ and $H_2$ over CuO-ZnO Catalysts Combined with Metal Oxides under 13 atm Pressure", Bull. Chem. Soc. Jpn., 64, 1991, pp. 1658–1663.

D. Gasser et al., "Hydrogenation of Carbon Dioxide over Copper-Zirconia Catalysts Prepared by In-Situ Activation of Amorphous Copper-Zirconium Alloy", Applied Catalysis, 48, 1989, pp. 279–294.

B. Denise et al., "Oxide-Supported Copper Catalysts Prepared from Copper Formate: Differences in Behaviour in Methanol Synthesis from CO/H$_2$ and CO$_2$/H$_2$ Mixtures", Applied Catalysis, 28, 1986, pp. 235–239.

Y. Amenomiya et al., "Copper-Zirconium Oxide Catalysts for the the Synthesis and Dehydrogenation of Methanol", Proceedings 9th Intl. Congress on Catalysis, vol. 2, Cl Chemistry, pp. 634–641.

Primary Examiner—W. J. Shine
Attorney, Agent, or Firm—Ladas & Parry

[57] ABSTRACT

A method of forming a methanol synthesis catalyst precursor comprises forming a precipitate comprising compounds, thermally decomposable to oxides or mixed oxides, of copper, zinc, aluminum and at least one element of Group IVB and/or Group VIIB of the Periodic Table of Elements.

18 Claims, 1 Drawing Sheet

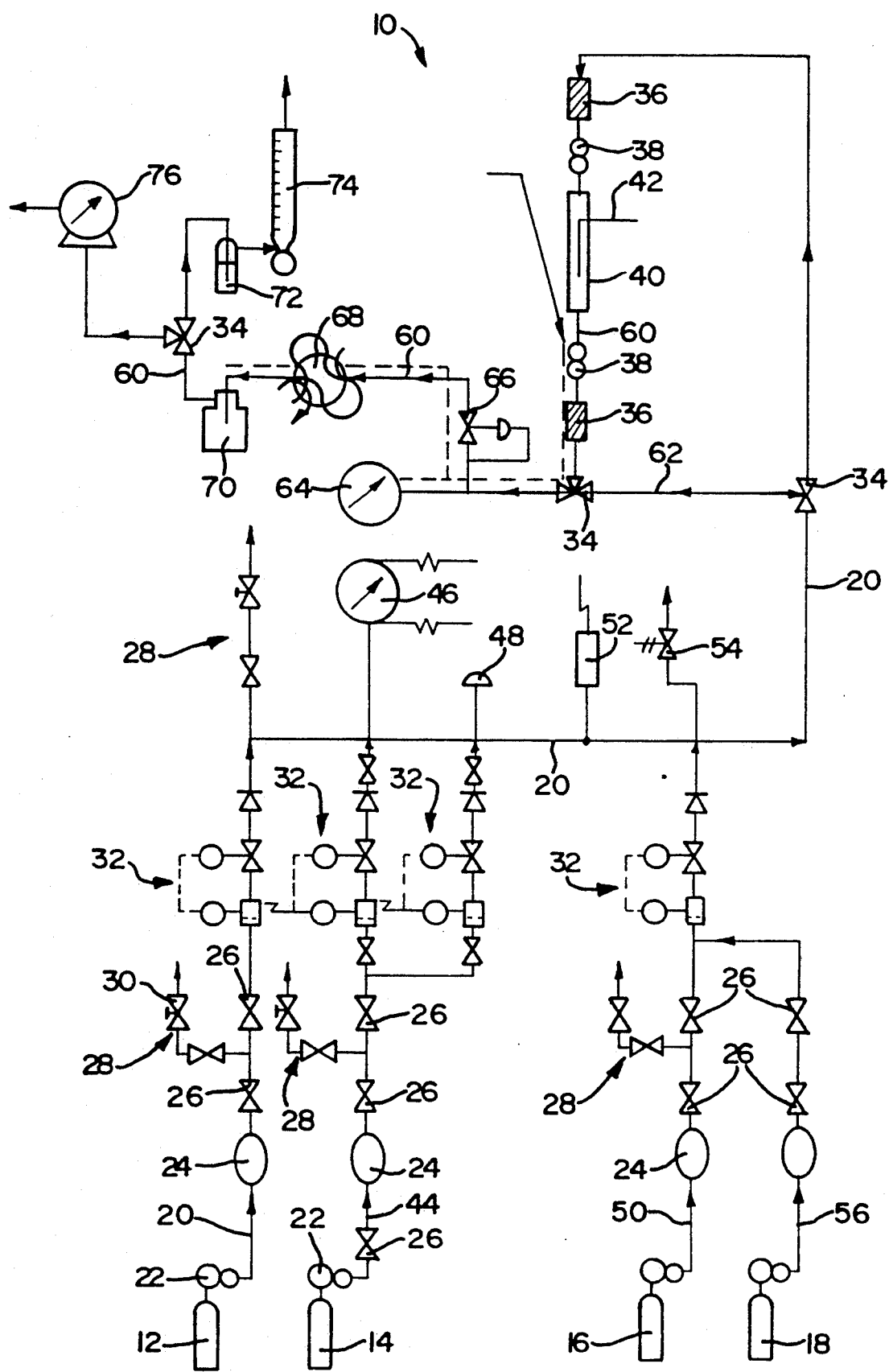

CATALYST FOR THE SYNTHESIS OF METHANOL

This invention relates to the synthesis of methanol. It relates in particular to a methanol synthesis catalyst precursor and to a method of forming such precursor; to a methanol synthesis catalyst and to a method of making such a catalyst; to an active methanol synthesis catalyst, and to a method of making thereof; and to a methanol synthesis process.

The production of methanol from synthesis gas comprising mixtures of hydrogen and carbon oxides in predetermined ratios, and derived from coal or natural gas, is known. These processes use copper-zinc-aluminum or copper-zinc-chromium mixed oxide catalysts. These catalysts exhibit relatively high activity and selectivity in low pressure synthesis of methanol using fixed-bed type reactors; however, their thermal stability and durability over long periods of time, their abrasion resistance, and their tolerance to catalyst poisons are generally low, so that they cannot be used in slurry type or fluidized bed reactors.

It is thus an object of the present invention to provide a methanol synthesis catalyst, in particular a low pressure methanol synthesis catalyst, whereby these drawbacks are at least reduced.

Thus, according to a first aspect of the invention, there is provided a method of forming a methanol synthesis catalyst precursor, which method comprises forming a precipitate comprising compounds, thermally decomposable to oxides or mixed oxides, of copper, zinc, aluminium and at least one element of Group IVB and/or Group VIIB of the Periodic Table of Elements.

The Periodic Table of Elements referred to is that in general usage, for example, that depicted on page 21 of Volume 10 of McGraw-Hill Encyclopedia of Science and Technology, 5th Edition, published in 1982 by McGraw-Hill Book Company.

The copper, zinc, aluminium and the element or transition metal of Group IVB and/or Group VIIB may initially be in the form of soluble compounds, preferably compounds which are soluble in an acid medium. Examples of such compounds are nitrate, formiate, carbonate, acetate, citrate and oxalate salts of the metals. Preferably, however, the elements are initially in their soluble nitrate form.

The element of Group IVB, when present, may be titanium, zirconium or hafnium, but zirconium is preferred. From Group VIIB, when present, manganese is preferred because of its ready availability. While the manganese can be used in solution in its nitrate form as hereinbefore described, it can instead be added as permanganate or as manganous acetate during granulation and prior to pelleting of the catalyst, as hereinafter described.

The precipitate may also include a compound, thermally decomposable to an oxide, of at least one element of Group VIB of the Periodic Table of Elements. This element may also initially be in the form of a soluble compound.

The element of Group VIB may initially be in the form of a thermally decomposable ammonium salt.

The element of Group VIB can thus be chromium, molybdenum or tungsten. Molybdenum is preferred in view of its promoter and poison removal capabilities, but chromium or tungsten will also give some benefit. The molybdenum may then be used in ammonium paramolybdate form which is readily soluble in ammonia-containing distilled water to form the thermally decomposable ammonium salt thereof.

The precipitate may be formed by admixing solutions of the elements; heating the resultant mixture to its precipitation temperature; heating a solution of a precipitant in water; and thereafter adding both solutions to preheated demineralized water with vigorous stirring and strict pH control, eg in a precipitation reactor.

Instead, the precipitate may be formed by admixing solutions of the elements; heating the resultant mixture to its precipitation temperature; and adding the preheated mixture or solution of elements rapidly to a predetermined or controlled volume of a preheated solution of a precipitant in water.

In yet another version of the invention, the precipitate may be formed by admixing solutions of the elements; heating the resultant mixture to its precipitation temperature; and adding a solution of precipitant in water, preheated to a predetermined precipitation temperature, to the hot solution or mixture of the elements, while stirring vigorously, until a predetermined pH value of the hot solution or mixture to which the precipitant solution is added, is reached.

The precipitate may then be separated from the residual liquid after allowing the liquid to stand under stirring and at the precipitation temperature for a period of time, eg for between 0.5 and 60 minutes, for maturation of the catalyst precursor. Where the precipitation reactor is used, the reactor vessel will thus naturally be allowed to stand under stirring as hereinbefore described. The separation may be effected by filtration.

The precipitate may be resuspended at least once, but typically a few times, in demineralized water, separated from the water by filtration, and finally washed thoroughly on the filter to remove as much alkali metal as possible The precipitant may be a solution of sodium, potassium and/or ammonium carbonate or bicarbonate in water.

The precipitation may be carried out at high temperature, eg between about 75° C. and 100° C. Lower temperatures, eg between about 50° C. and 60° C. may also be used, but the crystallite size of the catalyst precursor so formed is larger, and the activity of a catalyst formed therefrom, lower. The precipitation may be effected at a pH in the range of 6.5-9.5.

The washed precipitate comprising a homogeneous hydrated precursor may then be dried by any known drying process, for example in an oven at temperatures between 50° C. and 130° C., under vacuum or at normal pressure. Alternatively spray drying may be employed.

The dried precipitate or precursor thus obtained comprises an essentially homogeneous association of carbonates and hydroxycarbonates with a potential oxide content of between 65% and 80%.

According to a second aspect of the invention, there is provided a method of forming a methanol synthesis catalyst precursor, which method comprises forming a precipitate comprising compounds, thermally decomposable to oxides or mixed oxides, of copper, zinc, aluminium as well as at least one element of Group VIB of the Periodic Table of Elements.

As hereinbefore described, the copper, zinc and aluminium may initially be in soluble nitrate form, while the element of Group VIB may initially be in the form of a thermally decomposable ammonium salt. As also mentioned hereinbefore, the element of Group VIB may be molybdenum, which is initially in the form of ammonium paramolybdate which is readily soluble in ammonia-containing distilled water to form the thermally decomposable ammonium salt thereof. The precipitate may be formed as hereinbefore described with respect to the first aspect of the invention.

The invention extends also to a methanol synthesis catalyst precursor, when formed by one of the methods hereinbefore described.

According to a third aspect of the invention, there is provided a method of making a methanol synthesis catalyst, which comprises calcining a dried precursor as hereinbefore described.

The calcination may comprise treating the dried precipitate at a temperature of between 200° C. and 450° C., preferably between 250° C. and 350° C., for between 3 and 10 hours, to obtain a homogeneous catalyst. The catalyst comprising a homogeneous mixture of copper, zinc, aluminium, and elements of Groups IVB, VIB and VIIB as hereinbefore described still contains between 10% and 15% volatiles.

The homogeneous catalyst may be densified and pelletized after addition thereto of 1-3%, preferably about 2%, graphite to facilitate densification and pelleting.

The invention extends further to a methanol synthesis catalyst, when formed by the method as hereinbefore described.

According to a fourth aspect of the invention, there is provided a methanol synthesis catalyst, which comprises as a first component, an admixture of copper oxide and zinc oxide; and as a second component, an admixture of aluminium oxide and an oxide of an element of Group IVB of the Periodic Table of Elements and/or an oxide of an element of Group VIIB of the Periodic Table of Elements, with the first component being in intimate admixture with the second component.

As mentioned hereinbefore, the Group IVB element, when present, may be zirconium, while the Group VIIB element, when present, may be manganese.

The first component may also include an oxide of at least one element of Group VIB of the Periodic Table of Elements. The element of Group VIB, when present, may be molybdenum.

The first component which contains the copper in a highly dispersed form, after suitable reduction treatment of the catalyst to activate it, acts primarily as the active constituent of the resultant active catalyst, while the second component acts primarily but not exclusively as a structural support. The oxide of chromium, molybdenum and/or tungsten, when present, thus enhances the activity and/or selectivity of the catalyst and its resistance to poisons, while the zirconium oxide and/or manganese oxide enhances the stability, abrasion or attrition resistance, mechanical strength and thermal stability. Additionally, zirconium oxide and manganese oxide exhibit a substantial ability for improving the overall activity of the catalyst in methanol synthesis.

The catalyst may comprise, in terms of metal atoms, 30-70% copper, 20-50% zinc, 2-20% aluminium, 1-15% zirconium, 0.5-5% manganese and 0.1-1% molybdenum.

According to a fifth aspect of the invention, there is provided a method of making an active methanol synthesis catalyst, which comprises subjecting a catalyst as hereinbefore described to thermal activation treatment, to produce an active catalyst in which at least a portion of one or more of the copper, zinc, and, when present, element of Group VIB, is in metallic form.

The thermal activation may comprise reduction treatment of the calcined catalyst in situ after it has been charged into a methanol synthesis reactor, using a mixture of an inert gas, preferably nitrogen, and at least one reducing gas, such as hydrogen, carbon monoxide or a mixture thereof. The molar ratio between reducing gas and inert gas should be between 1:30 and 1:100. The reduction temperature may be between 100° C. to 280° C., preferably between 130° C. and 240° C., and the pressure may be 0.1 to 1 MPa.

The catalyst is preferably first slowly heated up under the inert gas and under a pressure of between 0.6–0.9 MPa, until a temperature of between 120° C. and 150° C. has been reached, using a temperature program, at a rate of between 30°–50° C./hour. Thereafter the reduction is allowed to take place by adding the reducing gas to the inert gas in a molar ratio as described above, but preferably between 1:50 and 1:40. The temperature is then slowly further increased using a second temperature program, at a rate of 15°–25° C./h to reach 190°–210° C. The thermal reductive activation is then continued at the temperature of 190°–210° C. for a time period of between 10 and 24 hours. Thereafter, in a final step, the temperature can be increased to between 230° C. and 250° C. and the molar ratio of reducing gas to inert gas to between 1:10 and 1:6 for a time period of 1-3 hours, in order to complete activation.

The invention extends also to an active methanol synthesis catalyst, when produced by the method as hereinbefore described.

According to a sixth aspect of the invention, there is provided a process of methanol synthesis, which comprises reacting carbon monoxide and/or carbon dioxide with hydrogen in the presence of an active methanol synthesis catalyst as hereinbefore described.

The methanol synthesis reaction may be conducted at a reaction temperature of between 180° C. and 300° C., and at a reactor pressure of between 3 and 12 MPa, preferably 4-10 mPa.

The synthesis gas may comprise (on a molar basis) 60-80% hydrogen, 5-30% carbon monoxide, 3-10% carbon dioxide, 0-5% methane and 0-10% inert gases, such as nitrogen, helium, argon and the like.

The gas hourly space velocity, i.e. the volume of the gas mixture (NTP) passed per volume of the catalyst bed per hour, may be from 2000 to 50000 v/vh, preferably from 4000 to 20000 v/vh.

As mentioned hereinbefore, methanol production, by means of catalysis, from synthesis gas, is known, and methanol is assuming increasing importance for the manufacture of synfuels, chemical feedstocks such as formaldehyde and specialty chemicals, as well as for its use for the production of fuel additives. To produce methanol efficiently and relatively inexpensively, it is thus desirable that methanol synthesis catalysts should not have the drawbacks set out hereinbefore, is the catalysts should have high catalytic activity, good heat resistance and durability, and good abrasion resistance. The catalysts of the present invention comply with these requirements.

Furthermore, catalysts for the low pressure methanol synthesis should also be tolerant to poisons such as sulphur and chlorine compounds or they should contain components which should preferably absorb these poisons, thus protecting the catalytically active components of the system for the methanol synthesis. Many methanol synthesis catalysts containing copper and zinc are highly sensitive to such poisons, and their catalytic performance may be severely restricted when the feed syngas contains rests of sulphur or chlorine. The catalysts of the present invention are, however, less sensitive to these poisons.

When activated and ready for use methanol synthesis should be of an essentially homogeneous composition, and should have an alkali concentration as low as possible. Iron contamination should also be avoided as far as possible not only because under the synthesis conditions this element may form iron carbonyls with the synthesis gas but also for its activity towards the formation of, Fischer-Tropsch products and the decrease in selectivity of the methanol synthesis reaction.

Still further, methanol synthesis catalysts should primarily consist of copper oxide crystallites not greater than 10 nanometers (100 Angstrom units) and preferably in the range 3.0-5.5 mm (30-55 Å). The specific surface area of the mentioned catalysts should vary between 50 and 160 m$^2$ g$^{-1}$. Again, the catalysts of the present invention comply with these requirements to a large degree.

The incorporation of several acidic or amphoteric oxides such as ceria, various rare earth oxides or a mixture thereof, lanthana, thoria, zirconia, alumina, titania or oxide combinations of a methanol synthesis catalyst may increase the tolerance of the catalytically active copper and zinc towards the poisons mentioned hereinbefore, as well as increase the activity of the resultant catalyst; however oxides of metals of the VIB Group, especially molybdenum as provided for in the present invention, show a particularly beneficial effect in regard to the poison resistance of the catalyst, particularly against sulphur, because of their higher affinity to this poison compared with copper.

The catalytic performance of known basic copper-zinc-aluminium catalyst is considered to be dependent on the formation of a bi-phasic precursor, i.e. a catalytically active phase containing copper stabilized by zinc oxide via an epitaxial growth mechanism and through free zinc oxide, and a zinc aluminate phase which gives good mechanical strength to the catalyst because of its refractory properties.

The aluminium content of the catalyst, while being of importance for its overall catalytic performance (especially as regards the mechanical properties of the catalytic systems), should be kept within limits (in most cases less than 10%, expressed as alumina). Higher alumina concentrations in the catalyst lead to the formation of acidic centres on the catalyst surface and to a dehydration of the product methanol to dimethylether with a simultaneous drop in the selectivity of the methanol synthesis. However, a decrease in the alumina content to less than 5% is detrimental to the overall stability of the catalyst and requires the addition of further structural promoters such as the amphoteric oxides of manganese, zirconium, and others.

BRIEF DESCRIPTION OF THE DRAWING

The invention will now be described by way of the following non-limiting examples, and with reference to the single FIGURE which shows schematically experimental apparatus for testing the catalysts of the examples:

EXAMPLE 1 (REFERENCE CATALYST)

Catalyst A (a basic low-pressure methanol synthesis catalyst) was prepared as follows:

Copper nitrate, $Cu(NO_3)_2.3H_2O$ (241.593 g) was dissolved in 2 l demineralized water to form a 0.5M solution (solution X). In a separate flask, zinc nitrate, $Zn(NO_3)_2.6H_2O$ (297.468 g) was dissolved in demineralized water (2 l) to form a 0.5M solution (solution Y). Aluminum nitrate, $Al(NO_3)_3.9H_2O$ (1500.516 g) was dissolved in 2 l demineralized water in a volumetric flask to form a 2M solution (solution Z). An aqueous 10% solution of sodium hydrogen carbonate, $NaHCO_3$, was produced by dissolving 500 g of the salt in 5 l demineralized water.

A solution comprising 371.7 ml of solution X, 180.7 ml of solution Y and 28.25 ml of solution Z was prepared and heated up to approximately 80° C. This solution was added concurrently with sufficient of the abovementioned 10% sodium bicarbonate solution (maintained at 80° C.) into a reactor vessel containing 500 ml preheated demineralized water (80° C.), under vigorous stirring, to ensure a slurry pH of 7.0±0.02 at all times. Precipitation commenced immediately and after precipitation was completed, the slurry was allowed to digest in the mother liquor at 80° C. and a pH of 7.0 for 1 hour. The precipitate was filtered off, washed thoroughly with 10 l hot (80°-90° C.) demineralized water to remove all traces of sodium ions, dried overnight at 110° C. and calcined at 350° C. for 5 hours, to produce a catalyst precursor.

After calcination of the Cu-Zn-Al catalyst precursor, the catalyst thus obtained (metal atom ratio Cu:Zn:Al=60.75:30.4:8.85 and having a specific surface area of 56 m$^2$/g) was pulverized and then subjected to compression moulding (pressure: 2.5 tonnes) to form tablets, which were in turn comminuted to a desired particle size. One gram of the Cu-Zn-Al catalyst in the form of crushed particles of size range 300-500 microns, i.e. 10$^{-6}$ meters, was loaded in a microreactor for methanol synthesis testing as hereinafter described.

This is not an example according to the present invention but is a comparative reference example.

EXAMPLE 2 (Reference Catalyst)

Catalyst B was prepared according to a procedure similar to that described in GB Patent 2047556:

134 g ammonium bicarbonate, $NH_4HCO_3$, was dissolved in 1130 ml demineralized water in a precipitation reactor. The solution was maintained at 30° C. under constant stirring. In a separate vessel 195 g copper nitrate, $Cu(NO_3)_2.3H_2O$, was dissolved in 1000 ml demineralized water and this solution was also maintained at 30° C. A solution comprising 9.65 g sodium aluminate ($NaAlO_2$) in 100 ml demineralized water was added under stirring to the copper nitrate solution. Finally, 49.4 zinc oxide, ZnO, were dissolved in 400 ml demineralized water and the resultant zinc oxide slurry stirred for 30 minutes at 30° C.

The aqueous solution containing the copper nitrate and the sodium aluminate was rapidly added to the ammonium bicarbonate solution, with constant stirring, and a precipitation reaction took place. A copper-aluminium slurry was thus formed and maintained at this temperature (30° C.). Finally, the zinc oxide slurry was added under vigorous stirring to the copper-aluminium slurry and thereafter a stream of gaseous carbon dioxide ($CO_2$) was bubbled into the slurry at a rate of 50 mol/min for 2 hours.

While continuing the bubbling of $CO_2$ gas, the temperature of the slurry was rapidly increased to 80° C. and maintained at this level for another 30 minutes. The resulting Cu-Zn-Al catalyst precursor was filtered, washed thoroughly with an excess of hot (80° C.) demineralized water, dried overnight and finally calcined following the same procedure as for catalyst A in Example 1 (350° C., 5 hours). After calcination, the resulting Cu-Zn-Al catalyst had a Cu:Zn:Al atom ratio of 54,5:42.15:3.35.

EXAMPLE 3

Catalyst AZr1.5 was prepared in an analogous procedure to the one described in Example 1: For approximately 25.375 g of the catalyst, 14.75 g CuO, 7.35 g ZnO, 2.88 g $Al_2O_3$, and 0.375 g $ZrO_2$ from the corresponding nitrate salt solutions were used. Thus, 372 ml of solution X were mixed with 181 ml of solution Y and 29 ml of solution Z. In this example, 26 ml of a 40 g/l $Zr(NO_3)_4.5H_2O$ were added to the above. The above quantities of the nitrate solutions were thoroughly mixed, preheated at 80° C. and then added via a dropping funnel, under vigorous stirring, to 500 ml preheated (80° C.) demineralized water simultaneously with sufficient $NaHCO_3$ solution to maintain a pH of 7. The catalyst precursor preparation was completed as in Example 1.

The calcined catalyst AZr1.5 was otherwise identical to catalyst A, except that it contained 1.5% $ZrO_2$ in addition to the quantities of CuO, ZnO, and $Al_2O_3$ specified in Example 1. The Cu:Zn:Al:Zr atom ratio was found to be 60.5:30.3:7.8:1.4, and its specific surface area was 66 $m^2/g$.

EXAMPLE 4

Example 3 was repeated except that the catalyst composition was changed in that, for the preparation of approximately 25.75 g catalyst, the amount of zirconium nitrate solution added was increased to 52 ml (hence corresponding to a total quantity of 0.75 g $ZrO_2$). The catalyst obtained was designated AZr3 and it contained 3% $ZrO_2$ in addition to the quantities of CuO, ZnO, and $Al_2O_3$ specified in Example 1. The Cu:Zn:Al:Zr atom ratio was found to be 59.6:29.9:7.7:2.8, and its specific surface area was 69 $m^2/g$.

EXAMPLE 5

Example 4 was repeated, save that the catalyst composition was further varied in that, for the preparation of approximately 26,25 g catalyst 86 ml of the above-mentioned zirconium nitrate solution (corresponding to 1.25 g $ZrO_2$) was added and hence the catalyst obtained, designated AZr5, contained 5% $ZrO_2$ in addition to the quantities of CuO, ZnO, and $Al_2O_3$ specified in Example 1. The resulting catalyst, after calcination, had a Cu:Zn:Al:Zr atom ratio of 58.5:29.3:7.6:4.6, with a specific surface area of 78 $m^2/g$.

EXAMPLE 6

The preparation of catalyst AZr3Mo was the same as in Example 4 except that 0.207 g $MoO_3$ as ammonium paramolybdate was added to the nitrates solution in order to prepare a catalyst promoted with 0.5% Mo, as $MoO_3$, in addition to the quantities of CuO, ZnO, $Al_2O_3$ and $ZrO_2$ specified in Example 4. The Cu:Zn:Al:Zr:Mo metal atom ratio of the resultant catalyst was 59.2:29.7:7.7:2.8:0.6. The specific surface area of the catalyst was found to be 99 $m^2/g$. The crystal size of copper therein was found to be 45 Å (using x-ray diffractrometry).

EXAMPLE 7

The preparation of catalyst AZr5Mo1 was the same as in Example 5 except that 0.207 g $MoO_3$ as an ammonium paramolybdate solution was added to the nitrates solution in order to prepare a catalyst promoted with 0.5% Mo as $MoO_3$ in addition to the quantities of CuO, ZnO, $Al_2O_3$ and $ZrO_2$ specified in Example 5. The Cu:Zn:Al:Zr:Mo metal atom ratio of the resultant catalyst was 58.2:29.1:7.5:4.6:0.6. A specific surface area of 126 $m^2/g$ was determined by BET. A copper crystallite size of 40 Å was measured by x-ray diffractrometry.

EXAMPLE 8

The procedure of preparation of Example 6 was repeated except that 0.25 g Mn as manganese nitrate solution was added to the other nitrates solution. The catalyst obtained was designated AZr3Mn1Mo1, and its Cu::Zn:Al:Mn:Zr:Mo metal atom raio was 58.5:29.3:7.5:1.2:2.8:0.7. The surface area was found to be 130 $m^2/g$, and its copper crystallite size 40 Å.

EXAMPLE 9

The procedure of preparation of Example 7 was repeated except that 0.25 g Mn as manganese nitrate solution was added to the other nitrates solution. The catalyst obtained was designated AZr5Mn1Mo1, and its Cu:Zn:Al:Mn:Zr:Mo metal atom ratio was 57.4:28.7:7.4:1.2:4.6:0.7. A specific surface area of 136 $m^2/g$ was determined by BET, and a copper crystallite size of 40 Å was found using x-ray diffractrometry.

EXAMPLE 10

The catalyst precursor of this example has the same composition as that obtained in Example 9; however the preparation procedure was different: 371.7 ml of solution X (see Example 1), 180.7 ml of solution Y, 28.25 ml of solution Z, 86 ml of the zirconium nitrate solution of Example 5 corresponding to 1.25 gm $ZrO_2$ and 5.75 ml of a manganese nitrate solution containing 0.25 g Mn were thoroughly mixed and then heated to 80° C. in an electric water bath, to produce Mixture A.

500 ml of deionized water were separately introduced into a precipitation reactor and heated up to 80° C. 700 ml of a 10% $NaHCO_3$ solution, also preheated to 80° C., were rapidly added to the reactor, together with 11.5 ml of an ammonium paramolybdate solution containing 0.207 g $MoO_3$. The pH after this addition was 8.9.

After reaching 80° C., the nitrates mixture (Mixture A) was added under vigorous stirring to the precipitation reactor. The time of precipitation was 1 minute. The precipitate was subsequently allowed to digest for 1 hour at 80° C. in the mother liquor. The pH fell initially to 6.5 but rose at the end of the 1 hour digestion period to reach a value of 7.00.

The contents of the precipitation reactor were then filtered through a sintered glass filter funnel, and the filter cake washed thoroughly with 10 litres boiling demineralized water. After filtration the catalyst precursor was dried overnight at 110° C. and then calcined at 300° C. for 7 hours.

The catalyst obtained was designated A2Zr5Mn1Mo1, and had the same composition as in Example 9;

however its method of preparation was different. The surface area of the above catalyst was found to be 140 m$^2$/g using BET, and its copper crystallite size was 40 Å using x-ray diffractrometry.

EXAMPLE 11

Catalyst A3Zr5Mn1 was prepared in an analogous procedure to that described in the previous examples. The proportion, however, of CuO:ZnO in the "active component", comprising 75% of the catalyst, was 30:70 by mass. The "supporting component" of the system consisting of Al$_2$O$_3$, ZrO$_2$ and MnO$_2$ in a ratio of 8.5:3:1, made up 25% of the catalyst (by mass). To make approximately 25 g of the catalyst, 5.625 g CuO, 13.125 g ZnO, 4.25 g Al$_2$O$_3$, 1.50 g ZrO$_2$ and 0.50 g MnO$_2$ from the corresponding nitrate salt solutions were mixed thoroughly together to make up 625 ml of solution X. This solution was then heated to 85° C. 850 ml of a 10% solution of K$_2$CO$_3$ (solution Y) were added into the precipitation reactor and preheated to 90° C. Finally, solution X, containing the nitrates, was rapidly added to solution Y in the precipitation reactor under vigorous stirring. The final pH was 7.5 and a precipitate having a light blue-green colour was formed. The precipitate was left to digest for 1 hour at 90° C. in the mother liquor. After an hour, a final pH of 8 was noted.

The contents of the precipitation reactor were then filtered according to the procedure described in the previous examples. The filter cake was first washed while on the filter using 2 liters boiling deionized water. Then, the filter cake was suspended in 2 liters boiling deionized water and refiltered. This procedure was repeated 3 times more, using a total of 10 liters deionized water. Finally, the catalyst precursor thus formed was dried for 16 hours at 110° C. and calcined at 280° C. for 6 hours. The calcined catalyst formed was suspended in 100 ml of a 1% solution of NH$_4$OH for 1 hour under slow stirring, dried at 110° C. for 1 hour, and calcined at 280° C. for an additional hour.

The final catalyst was found to have a BET surface area of 160 m$^2$/g, a specific copper surface area of 29 m$^2$/g, as measured by N$_2$O chemisorption, and a Cu crystallite size of 30 Å. The residual K content was less than 1 ppm.

The catalysts of Examples 1-11 were then tested using the experimental apparatus 10 shown schematically in the accompanying drawing, and the procedure described hereunder.

The experimental apparatus 10 comprises pressurized cylinders 12, 14, 16 and 18 containing CO, H$_2$, CO$_2$ and N$_2$ respectively.

From the cylinder 12 leads a flow line 20, fitted with a pressure regulator 22, a purifier and filter 24, solenoid valves 26, a vent line 28 fitted with a needle control valve 30, a mass flow controller 32, a further vent line 28, a three-way solenoid valve 34, a 20 micron filter 36, a quick connector 38, to a reactor 40 fitted with a thermocouple 42.

From the cylinder 14 leads a flow line 44, with the flow line 44 leading into the flow line 20 and being fitted with a regulator 22, valves 26, purifier and filter 24, flow controller 32, a pressure gauge 46 with minimum and maximum pressure alarms, and a capped spare liquid feed inlet 48.

From the cylinder 16 leads a flow line 50 fitted with a regulator 22, purifier and filter 24, valves 26, vent line 28, and flow controller 32. The line 50 leads into the line 20 downstream of a pressure transducer 52. The line 50 is also fitted with a pressure relief valve 54.

From the cylinder 18 leads a flow line 56 fitted with a regulator 22, purifier and filter 24, and valves 26.

A heated flow line 60 leads from the reactor 40 and is fitted with a quick connector 38, a filter 36, a three-way valve 34 (connected by means of a flow line 62 to the other three-way valve 34), a pressure gauge 64, a back-pressure regulator 66, a gas sampling valve 68, a condenser 70, a further three-way valve 34, a bubbler 72 and a soap-film flow meter 74. A flow line, fitted with a wet gas meter 76 leads from the last three-way valve 34, to vent.

The reactant gases (CO, CO$_2$ and hydrogen) as well as the nitrogen used for catalyst activation, were fed into the microreactor 40 after being purified. Brooks mass flow measuring and control systems 32 were used for individually controlling the flow rate of each gas and for establishing the gas mixtures required. The product stream from the reactor passed through the heated line 60 and after the pressure was reduced by a Tescom back-pressure regulator 66 the stream was sampled by an On-Line Carlo Erba gas chromatograph (not shown) equipped with a multi-port injection valve, through the valve 68. In all cases a reactant gas composition of 63.2% H$_2$, 31.9% CO and 4.9% CO$_2$ was used for methanol synthesis tests.

The mixture of carbon monoxide, carbon dioxide, methane, ethane, water and methanol was separated on a Porapak Q column while C$_1$-C$_{10}$ hydrocarbons, methanol, dimethyl ether and higher alcohols were analyzed simultaneously on a bonded OV-1 capillary column, using a temperature programme.

The procedure adopted for catalyst activation was similar to the one used in commercial methanol plants. The catalyst was slowly heated up to 130° C. (50° C./h) under a flow of nitrogen (4 L/Kg$_{cat}$/h). At this temperature, hydrogen was added to the nitrogen stream to a level of 2.5% and the temperature was further raised to 200° C. (20° C./h). The activation was continued for 16 h at this temperature. Thereafter the hydrogen concentration of the inert gas was further increased to 12% and the temperature was raised to 240° C. After 2 hours at this temperature the catalyst was ready for operation and the temperature was adjusted to 200° C. for the first test.

The various methanol synthesis catalysts prepared as described in the examples were suitably sized (300-500 μm) for charging to the micrometer. Thus, the catalyst powders obtained after calcination were pressed into tablets, crushed and sieved to size.

As measures of the catalytic activity, and for purposes of quantitative comparison with commercial results, the conversion of the feed carbon monoxide and the space-time-yield (STY) of the product methanol were used. STY is defined as follows:

Space-Time-Yield = Conversion × Selectivity × CO molar feed rate (Kg/Kg$_{cat}$/h).

The synthesis gas containing 31.9% CO, 4.9% CO$_2$ and 63.2% H$_2$ was contacted with the catalyst at a temperature in the range from 180°-325° C. However, operation of the process at temperatures above 300° C. tended to increase production of various by-products such as dimethylether, higher alcohols and gaseous hydrocarbons, at the expense of the selectivity to methanol. Thus, in order to obtain higher selectivities to methanol an operating temperature between 180° C. and 275° C. should be chosen. Nevertheless, tests above this temperature range (up to 325° C.) were carried out to demonstrate the improved thermal stability of the catalysts of the present invention in comparison with known catalysts.

The operating pressure is preferably in the range of 2.0–10.0 MPa and the gas hourly space velocity was varied over a wide range from 4000 to 20000 hour$^{-1}$. For comparison purposes though, in the comparative tests, a pressure of 4.0 MPa was used while the GHSV was maintained at a value of 8000 v/vh, except as otherwise specified.

The catalyst activity in the conversion of carbon monoxide to methanol and the selectivity of the product as well as the space-time-yield of methanol produced were then measured for the various catalysts prepared in the Examples, in comparative tests. These measures were performed after a suitable activation of the catalytic systems as hereinbefore described and the results are set out in Tables 1 to 4.

TABLE 3-continued
METHANOL SYNTHESIS RESULTS

| No. | CATALYST | EXAMPLE | SPACE-TIME-YIELD (1), (2) | |
|---|---|---|---|---|
| | | | 20 hours | 100 hours |
| 11. | A3Zr5Mn1 | 11 | 2.175*** | 2.100*** |

(1) Reaction conditions for tests 1–8 were: Temp.: 225° C., Pressure: 4.0 MPa, Gas Hourly Space Velocity: 8000 H$^{-1}$. Samples were evaluated after establishment of steady state conditions (20 hours). In some cases, in order to show the catalyst stability vs time-on-stream, long runs of 100 hours were carried out.
(2) Space-Time-Yields expressed as Kg$_{methanol}$/KG$_{cat}$/h
*Temp.: 225° C., Pressure: 5.0 MPa, GHSV: 18000 h$^{-1}$
**Temp.: 250° C., Pressure: 5.0 MPa, GHSV: 18000 h$^{-1}$
***Temp.: 250° C., Pressure: 7.5 MPa, GHSV: 20000 h$^{-1}$

EXAMPLE 12

Several of the catalysts described in Examples 3–11 were subjected to accelerated deactivation tests. After conducting the methanol synthesis for several hours (20 h) at reaction conditions typical for this reaction (5.0 MPa, 225° C., 8000 h$^{-1}$) relatively high reaction temperatures for the methanol synthesis (280° C.–300° C.) were applied for long time periods (100 h). Subsequently, the tests were conducted once again at the original reaction conditions (5.0 MPa, 225° C., 8000 h$^{-1}$). The results obtained are shown in Table 4:

TABLE 1
INITIAL YIELDS OF PRODUCTS OBTAINED IN METHANOL SYNTHESIS TESTS

| CATALYST | EXAMPLE No. | TEMP. (°C.) | CO | CO2 | CH4 | C$_2$/C$_2$= | C$_3$/C$_3$= | DME | MeOH | C$_4$/C$_4$= | C$_5$ | C$_6$ | C$_7$ |
|---|---|---|---|---|---|---|---|---|---|---|---|---|---|
| | | | | | | (all expressed in mol %) | | | | | | | |
| A | 1 | 225 | 85.72 | 2.435 | — | — | — | 0.283 | 11.524 | 0.040 | — | — | — |
| AZr1.5 | 3 | 225 | 77.20 | 1.540 | — | — | — | 0.755 | 20.506 | — | — | — | — |
| AZr3 | 4 | 225 | 74.81 | 2.774 | — | — | — | 0.453 | 21.677 | — | — | — | — |
| AZr5 | 5 | 225 | 73.20 | 3.506 | — | — | — | 0.706 | 22.590 | — | — | — | — |
| A3Zr5Mn1 | 11 | 225 | 70.01 | 2.753 | 0.200 | — | — | 0.688 | 26.588 | 0.190 | 0.120 | — | — |

Reaction conditions:
Pressure = 4.0 MPa, H$_2$:CO Ratio = 2:1, GHSV (STP): 8000 h$^{-1}$, Feed syngas: 31.9% CO, 4.9% CO$_2$ in H$_2$.

TABLE 2
INITIAL CARBON MONOXIDE CONVERSION IN (%)

| RUN No. | TEMP. (°C.) | BASIC Cu/Zn/Al CATALYST (A) (EXAMPLE 1) | Cu/Zn/Al CATALYST +1.5% ZrO$_2$ (AZr1.5) (EXAMPLE 3) | Cu/Zn/Al CATALYST +3% ZrO$_2$ (AZe3) (EXAMPLE 4) | Cu/Zn/Al CATALYST +5% ZrO$_2$ (AZr5) (EXAMPLE 5) |
|---|---|---|---|---|---|
| 1. | 200 | 3.52 | 7.16 | 8.94 | 10.85 |
| 2. | 225 | 14.28 | 22.80 | 25.19 | 26.80 |
| 3. | 250 | 26.20 | 28.92 | 30.44 | 31.97 |
| 4. | 275 | 30.73 | 31.89 | 33.52 | 33.24 |
| 5. | 300 | 33.06 | 34.58 | 38.01 | 37.66 |
| 6. | 325 | 39.64 | 40.22 | 41.63 | 43.55 |

Reaction Conditions:
Pressure = 4.0 MPa, H$_2$:CO Ratio = 2:1, GHSV (STP): 8000 h$^{-1}$
Feed syngas: 31.9% CO, 4.9% CO$_2$ in H$_2$.

TABLE 3
METHANOL SYNTHESIS RESULTS

| No. | CATALYST | EXAMPLE | SPACE-TIME-YIELD (1), (2) | |
|---|---|---|---|---|
| | | | 20 hours | 100 hours |
| 1. | A | 1 (Ref.) | 0.440 | |
| 2. | B | 2 (Ref.) | 0.531 | |
| 3. | AZr1.5 | 3 | 0.784 | |
| 4. | AZr3 | 4 | 0.829 | |
| 5. | AZr5 | 5 | 0.864 | 0.854 |
| 6. | AZr3Mo | 6 | 0.870 | |
| 7. | AZr5Mo1 | 7 | 0.920 | 0.905 |
| 8. | AZr5Mn1Mo1 | 9 | 1.050 | 1.025 |
| 9. | A2Zr5Mn1Mo1 | 10 | 1.205* | 1.155* |
| 10. | A2Zr5Mn1Mo1 | 10 | 1.500** | |

TABLE 4

| No. | CATALYST | EXAMPLE | SPACE-TIME-YIELD (1), (2) | | |
|---|---|---|---|---|---|
| | | | 1–20 h* | 20–120 h** | 120–130 h* |
| 1. | AZr5 | 5 | 0.860 | 0.875 | 0.836 |
| 2. | AZr5Mo1 | 7 | 0.920 | 0.942 | 0.895 |
| 3. | AZr5Mn1Mo1 | 9 | 1.050 | 1.075 | 1.025 |
| 4. | A2Zr5Mn1Mo1 | 10 | 1.200 | 1.350 | 1.155 |
| 5. | A3Zr5Mn1 | 11 | 1.325 | 1.500 | 1.310 |

(1) Reaction conditions for tests 1–3 were:
Temp: 225° C., Pressure: 4.0 MPa, GHSV (STP): 8000 h$^{-1}$.
Reaction conditions for tests 4–5 were:
Temp: 225° C., Pressure: 5.0 MPa, GHSV (STP): 18000 h$^{-1}$.
(2) Space-Time-Yields expressed as Kg$_{methanol}$/Kg$_{cat}$/h
*Reaction temperature for 1–20 and 120–130 hours-on-stream: 225° C.
**Reaction temperature for 20–120 hours-on-stream: 280° C.

The catalysts in accordance with the invention generally exhibit improved catalytical activity at very low and very high reaction temperatures for the methanol synthesis, as compared to the reference catalysts, as is evident from Table 2. A further advantage of the catalysts of the invention is that they demonstrate enhanced mechanical stability and attrition resistance as compared to the reference catalysts, which renders them suitable for other methanol synthesis processes, e.g. fluidized bed and slurry reactor operation. The presence of the molybdenum enhances catalyst resistance to poisons such as sulphur and chlorine.

I claim:

1. A methanol synthesis catalyst precursor which comprises an intimate admixture of precipitated compounds, which are thermally decomposable to oxides or mixed oxides, of copper, zinc, aluminium, zirconium, and molybdenum.

2. A catalyst precursor according to claim 1, wherein the intimate admixture of precipitated compounds is obtained by admixing solutions of soluble salts of copper, zinc, aluminium, and the other elements; heating the resultant mixture to its precipitation temperature; heating an aqueous solution of a precipitant selected from sodium, potassium or ammonium carbonate or bicarbonate; adding the mixture and the aqueous solution concurrently to preheated demineralized water with stirring; controlling the pH between 6.5 and 9.5, and the temperature at a value between about 75° C. and 100° C. while the compounds precipitate; allowing the liquid to stand under stirring and at said temperature for a period of time for maturation of the precipitated compounds; separating the intimate admixture of precipitated compounds from the residual liquid; resuspending the admixture of precipitated compounds at least once in water; separating the admixture of precipitated compounds from the water; thereafter finally washing the admixture of precipitated compounds; and drying the admixture, with the intimate admixture of the precipitated compounds comprising an essentially homogeneous association of carbonates and hydroxycarbonate with a potential oxide content of between 65% and 80%.

3. A catalyst precursor according to claim 1, wherein the intimate admixture of precipitated compounds is obtained by admixing solutions of soluble salts of copper, zinc, aluminium, and the other elements; heating the resultant mixture to its precipitation temperature; adding the preheated mixture rapidly to a preheated aqueous solution of a precipitant selected from sodium, potassium or ammonium carbonate or bicarbonate; controlling the pH between 6.5 and 9.5, and the temperature at a value between about 75° C. and 100° C. while the compounds precipitate; allowing the liquid to stand under stirring and at said temperature for a period of time for maturation of the precipitated compounds; separating the intimate admixture of precipitated compounds from the residual liquid; resuspending the admixture of precipitated compounds at least once in water; separating the admixture of precipitated compounds from the water; thereafter finally washing the admixture of precipitated compounds; and drying the admixture, with the intimate admixture of the precipitated compounds comprising an essentially homogeneous association of carbonates and hydroxycarbonate with a potential oxide content of between 65% and 80%.

4. A catalyst precursor according to claim 1, wherein the intimate admixture of precipitated compounds is obtained by admixing solutions of soluble salts of copper, zinc, aluminium, and the other elements; heating the resultant mixture to its precipitation temperature, adding an aqueous solution of a precipitant selected from sodium, potassium or ammonium carbonate or bicarbonate, preheated to said precipitation temperature, to the hot mixture with stirring, until a pH value of the hot mixture of between 6.5 and 9.5 is reached; controlling the pH between 6.5 and 9.5, and the temperature at a value between about 75° C. and 100° C. while the compounds precipitate; allowing the liquid to stand under stirring and at said temperature for a period of time for maturation of the precipitated compounds; separating the intimate admixture of precipitated compounds from the residual liquid; resuspending the intimate admixture of precipitated compounds at least once in water; separating the admixture of precipitated compounds from the water; thereafter finally washing the admixture of precipitated compounds; and drying the admixture, with the intimate admixture of the precipitated compounds comprising an essentially homogeneous association of carbonates and hydroxycarbonates with a potential oxide content of between 65% and 80%.

5. A catalyst precursor according to claim 1 which includes at least one element of Group VIIB of the Periodic Table of Elements.

6. A catalyst precursor according to claim 5 wherein the element of Group VIIB is manganese.

7. A catalyst precursor according to claim 6, which comprises, in terms of metal atoms, 30–70% copper, 20–50% zinc, 2–20% aluminium, 1–15% zirconium, 0.5–5% manganese, and 0.1–1% molybdenum.

8. A methanol synthesis catalyst precursor which comprises an intimate admixture of precipitated compounds, which are thermally decomposable to oxides or mixed oxides, of copper, zinc, aluminium, zirconium, and manganese.

9. A catalyst precursor according to claim 8 which includes at least one element of Group VIB of the Periodic Table of Elements.

10. A methanol synthesis catalyst which comprises pellets of calcined precipitated compounds, which are in intimate admixture and which are thermally decomposable to oxides or mixed oxides, of copper, zinc, aluminium, zirconium, and molybdenum.

11. A catalyst according to claim 10, wherein the pellets of calcined precipitated compounds are obtained by admixing solutions of soluble salts of copper, zinc, aluminium, and the other elements; heating the resultant mixture to its precipitation temperature; heating an aqueous solution of a precipitant selected from sodium, potassium or ammonium carbonate or bicarbonate; adding the mixture and the aqueous solution concurrently to preheated demineralized water with stirring; controlling the pH between 6.5 and 9.5, and the temperature at a value between about 75° C. and 100° C. while the compounds precipitate; allowing the liquid to stand under stirring and at said temperature for a period of time for maturation of the precipitated compounds; separating the intimate admixture of precipitated compounds thus formed from the residual liquid; resuspending the admixture of precipitated compounds at least once in water; separating the admixture of precipitated compounds from the water; thereafter finally washing the admixture of precipitated compounds; drying the admixture with the intimate admixture of the precipitated compounds comprising an essentially homogeneous association of carbonates and hydroxycarbonate with a potential oxide content of between 65% and 80%; calcining the dried admixture of precipitated compounds at a temperature between 200° C. and 450° C. for between 3 and 10 hours; adding 1-3% graphite thereto; and densifying and pelletizing the intimate admixture of compounds.

12. A catalyst according to claim 10, wherein the pellets of calcined precipitated compounds obtained by admixing solutions of soluble salts of copper, zinc, aluminium, and the other elements; heating the resultant mixture to its precipitation temperature; adding the preheated mixture rapidly to a preheated aqueous solution of a precipitant selected from sodium, potassium or ammonium carbonate or bicarbonate; controlling the pH between 6.5 and 9.5, and the temperature at a value between about 75° C. and 100° C. while the compounds precipitate; allowing the liquid to stand under stirring and at said temperature for a period of time for maturation of the precipitated compounds; separating the intimate admixture of precipitated compounds thus formed from the residual liquid; resuspending the admixture of precipitated compounds at least once in water; separating the admixture of precipitated compounds from the water; thereafter finally washing the admixture of precipitated compounds; and drying the admixture with the intimate admixture of the precipitated compounds comprising an essentially homogeneous association of carbonates and hydroxycarbonate with a potential oxide content of between 65% and 80%; calcining the dried admixture of precipitated compounds at a temperature between 200° C. and 450° C. for between 3 and 10 hours; adding 1-3% graphite thereto; and densifying and pelletizing the intimate admixture of compounds.

13. A catalyst according to claim 10, wherein the pellets of calcined precipitated compounds are obtained by admixing solutions of soluble salts of copper, zinc, aluminium, and the other elements; heating the resultant mixture to its precipitation temperature, adding an aqueous solution of a precipitant selected from sodium, potassium or ammonium carbonate or bicarbonate, preheated to said precipitation temperature, to the hot mixture with stirring, until a pH value of the hot mixture of between 6.5 and 9.5 is reached; controlling the pH between 6.5 and 9.5, and the temperature at a value between about 75° C. and 100° C. while the compounds precipitate; allowing the liquid to stand under stirring and at said temperature for a period of time for maturation of the precipitated compounds; separating the intimate admixture of precipitated compounds thus formed from the residual liquid; resuspending the admixture of precipitated compounds at least once in water; separating the admixture of precipitated compounds from the water; thereafter finally washing the admixture of precipitated compounds; and drying the admixture with the intimate admixture of the precipitated compounds comprising an essentially homogeneous association of carbonates and hydroxycarbonate with a potential oxide content of between 65% and 80%; calcining the dried admixture of precipitated compounds at a temperature between 200° C. and 450° C. for between 3 and 10 hours; adding 1-3% graphite thereto; and densifying and pelletizing the intimate admixture of compounds.

14. A methanol synthesis catalyst according to claim 10 which includes an element of Group VIIB of the Periodic Table of Elements.

15. A catalyst according to claim 14 wherein the element of Group VIIB is manganese.

16. A catalyst according to claim 15, which comprises, in terms of metal atoms, 30-70% copper, 20-50% zinc, 2-20% aluminium, 1-15% zirconium, 0.5-5% manganese, and 0.1-1% molybdenum.

17. A methanol synthesis catalyst which comprises pellets of calcined precipitated compounds, which are in intimate admixture and which are thermally decomposable to oxides or mixed oxides, of copper, zinc, aluminium, zirconium, and manganese.

18. A catalyst according to claim 17 which includes at least one element of Group VIB of the Periodic Table of Elements.

* * * * *